United States Patent [19]
Laswick et al.

[11] Patent Number: 6,055,981
[45] Date of Patent: May 2, 2000

[54] AUTOMATIC TRANSPORT VENTILATOR WITH MONITORING ALARMS

[75] Inventors: Ronald A Laswick, Brampton; Kevin D. J. Bowden, Orangeville; Helmut Zauner, Stouffville; Tian X. Zhao; Tarek A. F. Arafat, both of Mississauga, all of Canada

[73] Assignee: O-Two Systems International, Inc., Canada

[21] Appl. No.: 09/039,490

[22] Filed: Mar. 16, 1998

[51] Int. Cl.[7] .............................. A61M 16/00; A62B 9/02
[52] U.S. Cl. ................... 128/204.18; 128/204.26; 128/205.24
[58] Field of Search ............... 128/204.18, 204.25, 128/204.26, 205.24, 202.22

[56] References Cited

U.S. PATENT DOCUMENTS

| | | | |
|---|---|---|---|
| 3,762,439 | 10/1973 | Heath | 137/549 |
| 4,766,894 | 8/1988 | Legrand et al. | 128/204 |
| 4,825,802 | 5/1989 | Le Bec | 116/70 |
| 5,360,000 | 11/1994 | Carter | 128/205.24 |
| 5,520,170 | 5/1996 | Laswick et al. | 128/204.18 |
| 5,640,149 | 6/1997 | Campbell | 128/204.21 |
| 5,665,894 | 9/1997 | Baker | 73/1.05 |
| 5,692,497 | 12/1997 | Schnitzer et al. | 128/204.21 |
| 5,765,554 | 6/1998 | Somerson et al. | 128/204.18 |
| 5,881,717 | 3/1999 | Isaza | 128/204.21 |
| 5,921,238 | 7/1999 | Bourdon | 128/204.23 |

FOREIGN PATENT DOCUMENTS

| | | |
|---|---|---|
| 2 597 202 | 10/1987 | France . |
| 2 601 877 | 1/1988 | France . |

*Primary Examiner*—John G. Weiss
*Assistant Examiner*—Todd Martin
*Attorney, Agent, or Firm*—Parkhurst & Wendel, L.L.P.

[57] ABSTRACT

An automatic resuscitation device for administering a breathable gas under pressure to a patient by an operator where all operating controls and alarms are powered by the pressurized gas in a manual override mode, a patient breathing deemed override mode, and an automatic mode. The device uses no power source other than the pressurized gas to drive alarms and the entire control system. The controls include pneumatic valves and pneumatic alarms as follows: a breathing circuit integrity alarm for notifying the operator that an integrity condition has been detected; a power fail alarm for notifying the operator that the source of pressurized gas has a pressure below a selected source input valve; and pressure relief alarm for notifying the operator that the patient's airway is above the selected pressure relief value.

13 Claims, 6 Drawing Sheets

AUTOMATIC TRANSPORT VENTILATOR WITH MONITORING ALARMS

TECHNICAL FIELD

The invention is directed to an automatic transport ventilator for administering a breathable gas under pressure to a patient, having controls completely operated under the power of the pressurized gas, and in particular having gas powered alarms which notify the operator of a change in operation, failure or dangerous condition.

BACKGROUND OF THE ART

In the relevant field of patient transport ventilators, a wide range of devices to aid breathing are known. The invention relates to an automatically operated transport ventilator typically used in trauma situations by hospital and ambulance crews, firefighters, military medics, and the like during life threatening emergencies.

Simple transport ventilators amount to a hand held mask fitted over the patient's nose and mouth, with a manual valve to control breathable gas flow from a pressurized source of gas. Typically pure oxygen is provided in portable metal cylinders or from built-in gas conduits in a hospital setting for example. Air is optionally mixed with the oxygen through an in-line venturi mixer.

The prior art includes several advanced means to control and monitor the flow of breathable gas under pressure between the gas source and the patient mask. Since the patient may be in different states, i.e.: unconscious and not breathing; breathing sporadically; or breathing independently, and may shift between such states unpredictably, manual control means which require constant operator attention and control are not preferred.

A fully automatic transport ventilator is described in U.S. Pat. No. 5,520,170 by the present inventors, for example. The obvious advantages of full automation include lowering the level of training and competence of the operator, and enabling the operator to concentrate fully on other emergency duties while resuscitation proceeds untended.

A disadvantage of such automatic devices however is the danger inherent in a lack of supervision. For example, several dangerous conditions may arise suddenly or the operator may desire notification of changes in the patient's condition.

If the supply of breathable gas is depleted, the patient may suffocate due to the air tight nature of the mask and the automatic device may cease to operate. If the mask leaks or becomes dislodged, the patient does not receive the intended gas flow and pressure for optimum resuscitation. If the pressure of gas supplied to the patient is too high, the patient's lungs may be damaged, whereas if the gas supply pressure is too low, the resuscitation does not proceed as intended.

It is desirable therefore to produce an automatic transport ventilator device that includes means to control and monitor the device, as well as to notify the operator of various important changes in the status of the patient and device. In particular it is desirable to provide such functionality with a minimum of additional operator training and mechanical complexity.

DISCLOSURE OF THE INVENTION

The invention provides a novel transport ventilator device for administering a breathable gas under pressure to a patient by an operator. The device has all operating controls and alarms powered by the pressurized gas in a manual override mode, a patient breathing demand override mode, and an automatic mode.

The device includes a housing enclosing a patient breathing circuit comprising: a gas accumulation chamber; a breathing chamber; breathing check valve means therebetween for permitting one way passage of inhaled gas from the accumulation chamber to the breathing chamber; and exhale check valve means for permitting passage of patient exhaled breath from the breathing chamber to atmosphere external to the device.

A pressure regulator is used to admit gas into the device from a source of pressurised gas. Gas distribution circuits distribute gas between the regulator outlet and the gas accumulation chamber selectively via a manual circuit, a demand circuit and an automatic circuit.

Gas pressure operated control means, powered solely by the pressure differential between the pressurised gas from the regulator input port means and atmospheric pressure external to the device, monitor and control the gas distribution circuit.

Of particular note, the control means include alarms as follows: a breathing circuit integrity alarm for notifying the operator that an integrity condition has been detected; power fail alarm for notifying the operator that the source of pressurised gas has a pressure below a selected source input value; and pressure relief alarm for notifying the operator that the patient's airway is above the selected pressure relief value.

The alarms provide an added degree of safe operation to automatically notify operators under extreme stress and urgent conditions. The use of readily available gas pressure as a source of power for the alarms and related control system results in a simple reliable enhancement.

In contrast the alternative of adding complex electric powered components would require a further electric power source such as a battery. Addition of electric components adds an explosion hazard when used in conjunction with oxygen gas. Use of batteries increase the weight of the device, and add the burden of recharging, replacement and power level monitoring.

In short, the simpler the better. This is especially true where rescue operators are extremely busy, stressed and otherwise completely preoccupied with life threatening situations. A preference for a completely automatically operated transport ventilator with fail-safe alarms requiring little maintenance and supervision is understandable.

Use of available gas pressure as a power source has significant advantage over relatively complex electrical alternatives. The operators must in any case ensure that sufficient gas pressure is always available to administer gas to the patient during resuscitation. The use of gas powered controls and alarms add no further burden to the operator. In contrast, electric alarms and controls add a further layer of complexity to the device in manufacture, maintenance and operation.

Further details of the invention and its advantages will be apparent from the detailed description and drawings included below.

BRIEF DESCRIPTION OF THE DRAWINGS

In order that the invention may be readily understood, one preferred embodiment of the invention will be described by way of example, with reference to the accompanying drawings wherein:

FIGS. 4, 5, and 6 are detail views of typical components used in several different locations in the distribution and control circuits wherein:

DETAILED DESCRIPTION OF PREFERRED EMBODIMENTS

Due to the complexity of the various circuits and controls, a brief general description of the device and its operation will be presented first, with a more detailed description to follow.

Breathing Circuit

Figure 1:
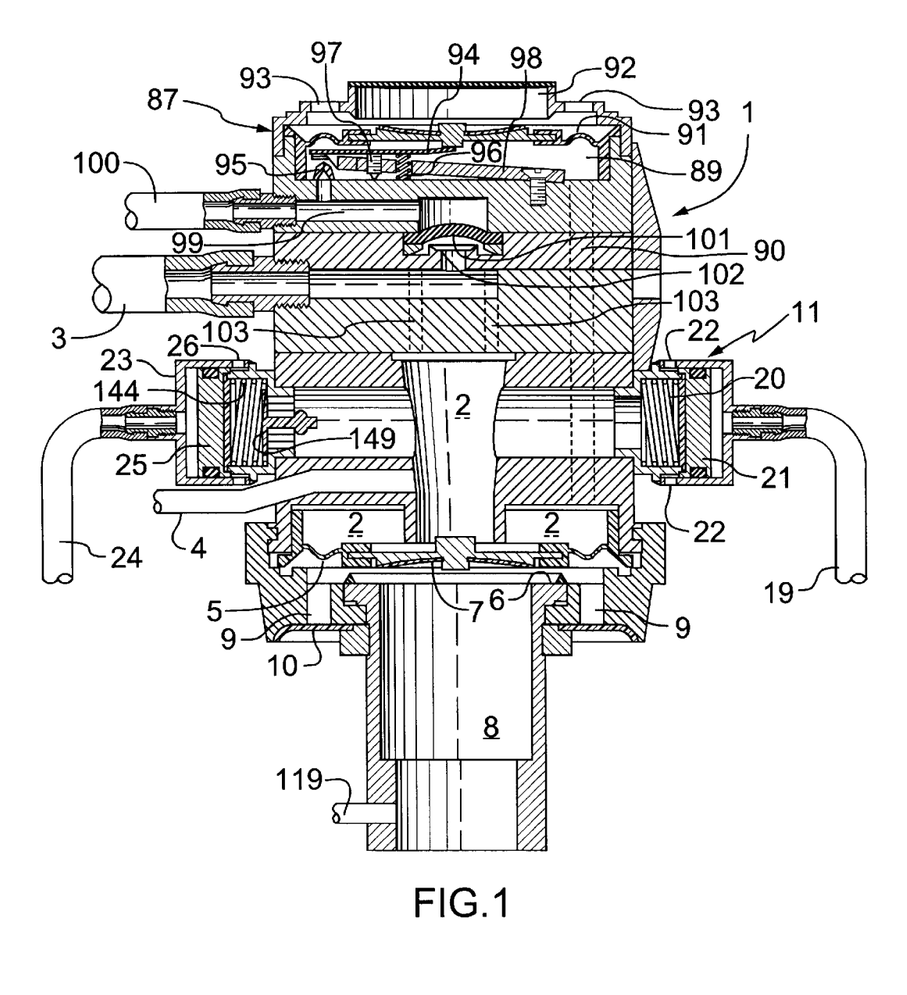
FIG. 1 is a sectional view through the housing which delivers breathable gas to a patient mask via the conduit at the lower end of the housing as drawn.

FIG. 1 shows a sectional view through the main housing 1 that encloses the patient breathing circuit. The device is powered by pressurized breathable gas to provide gas to the patient in the following modes:

manual override mode where the operator manually controls the supply of gas;

patient breathing demand override mode where the breathing action of the patient serves to override the automatic timed distribution of gas to the patient; and automatic mode where pressurized gas is supplied in a timed inhale-exhale sequence according to preselected parameters.

Breathable gas is supplied to a gas accumulation chamber 2 in the housing 1. In patient breathing demand mode gas is supplied from demand supply conduit 3. In automatic mode and manual override mode, gas is supplied from the automatic supply conduit 4. The details of gas supply and controls will be explained later.

Pressurized gas accumulates in the accumulation chamber 2, forcing the flexible rubber annulus 5 of the breathing check valve downwardly, to engage the valve seat 6. This engagement closes off gas passage through the exhale ports 9 and flexible exhale flapper check valve 10.

Flapper valve 7 opens due to higher relative pressure in the accumulation chamber 2 and permits one way passage of inhaled gas from the accumulation chamber 2 to the breathing chamber 8. The breathing chamber 8 is mounted to a conventional flexible face mask (not shown) that is secured over the mouth and nose of the patient.

The gas pressure in the breathing chamber 8 then equalizes and exceeds the gas pressure in the accumulation chamber 2. This pressure buildup in the breathing chamber 8 results either in demand mode from the force of the patient exhaling independently, or in automatic/manual mode due to automatic/manual shut off of gas supply to the accumulation chamber 2 and elastic rebound of the patient's flexible lung-rib cage structure. In either case, the higher relative pressure in the breathing chamber 8 then forces the flapper 7 shut, forces the flexible annulus 5 upwards, disengages the annulus 5 from the valve seat 6 and opens a path to the exhale ports 9 permitting passage of exhaled breath from the breathing chamber 8 through the exhale check valve 10 to atmosphere external to the device.

An emergency air intake valve 11 provides air to the accumulation chamber 2 in the event that gas supply pressure is dangerously low and there is a risk that the patient may suffocate under the face mask.

Figure 2:
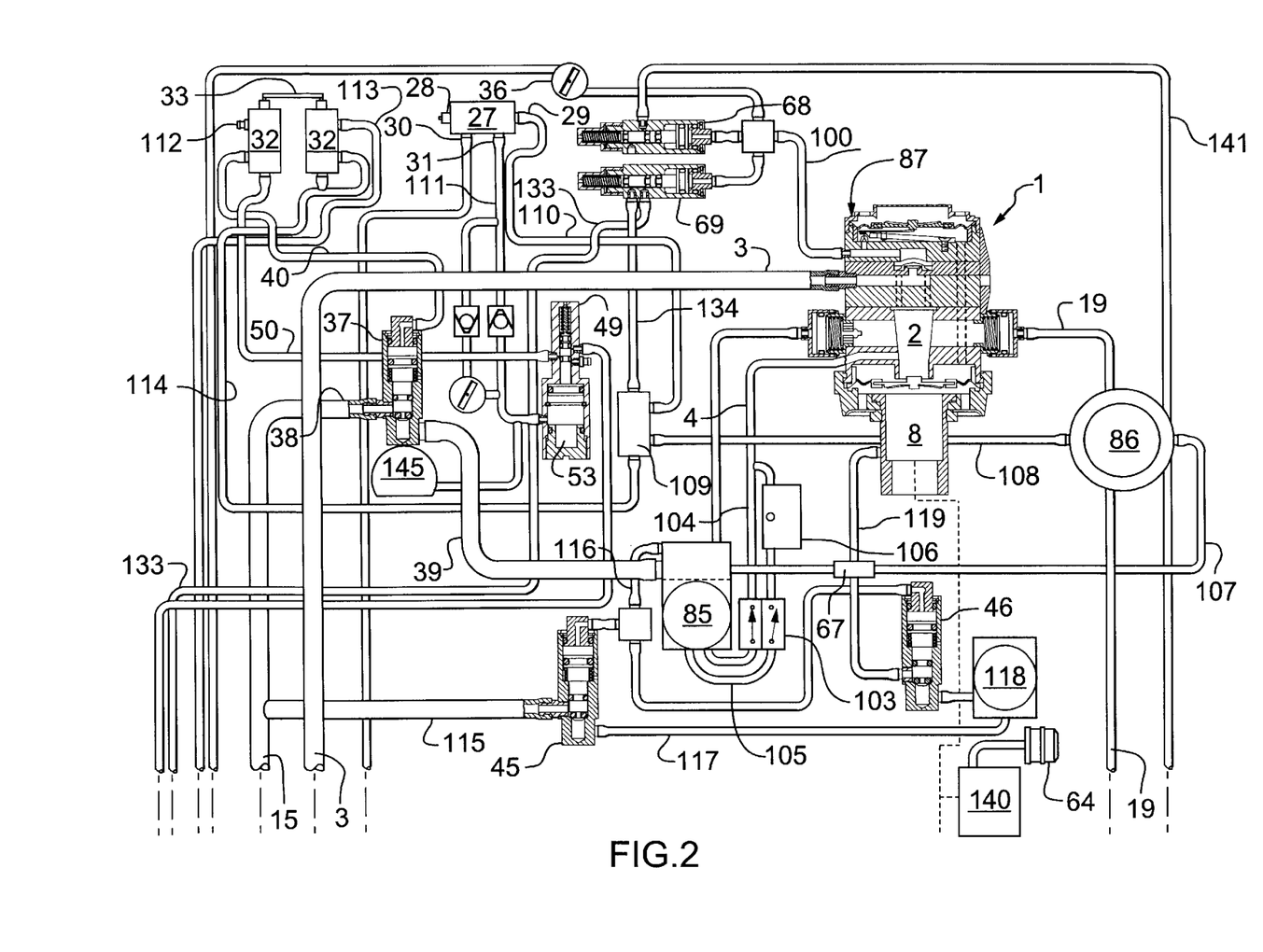
FIGS. 2 and 3 are a schematic circuit diagram showing the housing, the gas input pressure regulator, with the gas distribution circuits, control circuits and alarms therebetween.
Figure 3:
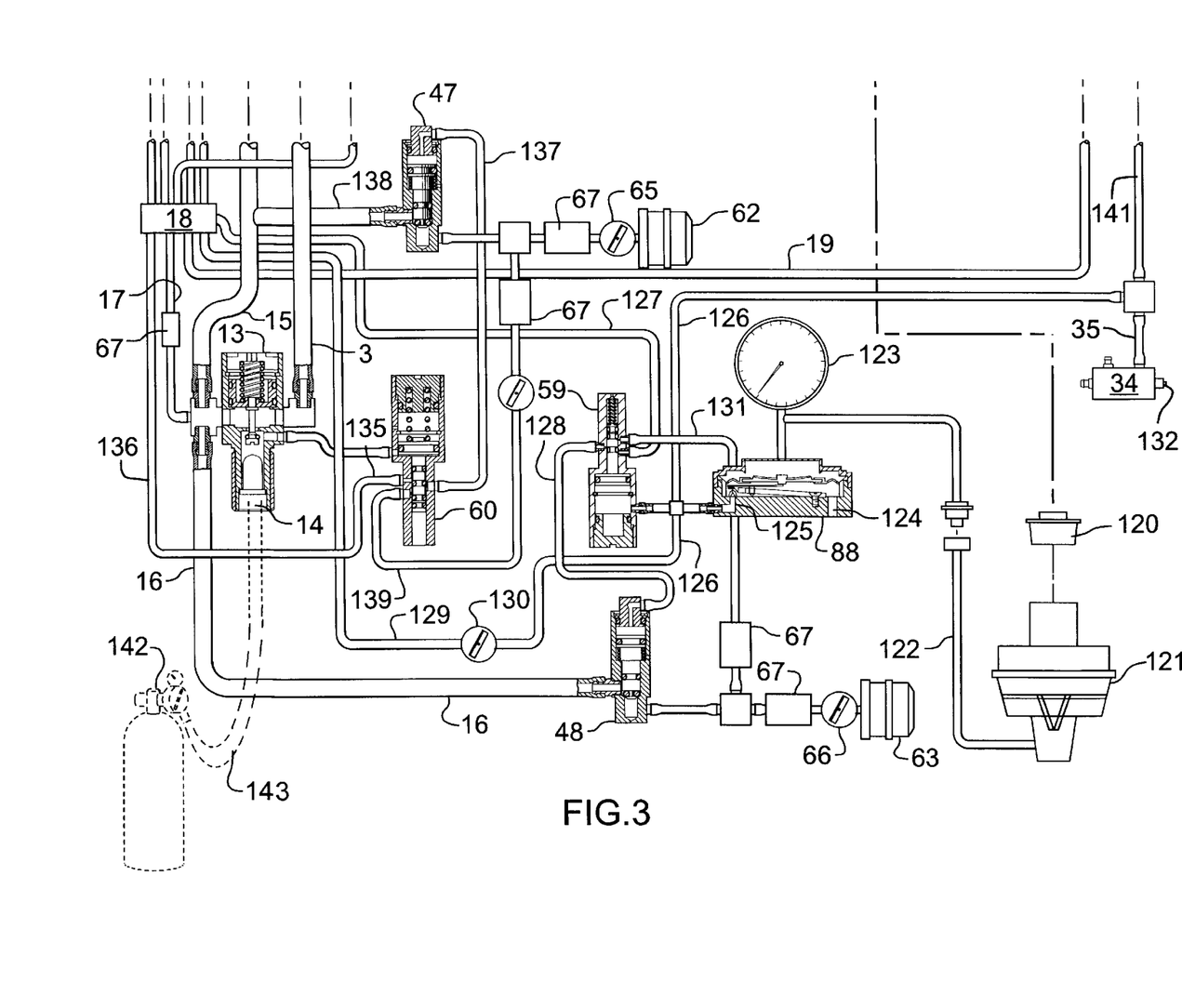

Brief reference is made to the overall schematic views of FIGS. 2 and 3. The source of breathable gas is shown as a standard cylinder 12 (in dashed outline) that contains pressurized oxygen gas for example. The cylinder 12 includes a conventional external regulator 142 and flexible supply hose 143. A second internal regulator 13 is provided to ensure accuracy of inlet pressure since many conventionally used regulators do not maintain pressure reliably as the supply of gas depletes. The internal pressure regulator 13 admits gas into the transport ventilator device via input port 14. The regulator has two lateral output ports feeding gas to relatively large supply conduits as follows: demand supply conduit 3; automatic supply conduit 15; and breathing circuit integrity alarm supply conduit 16. In addition a relatively small control manifold conduit 17 supplies gas to a control manifold 18 that supplies gas to various control circuits of the device.

When the gas pressure supplied from the cylinder 12 is depleted, the gas pressure is also reduced in manifold 18 and emergency control conduit 19. Referring again to FIG. 1, the emergency air intake valve 11 allows air from outside the device to enter the accumulation chamber 2 as follows. Coil spring 20, forces piston 21 towards the right as drawn when gas pressure in conduit 19 is below a preselected value. As a result, air can enter via vents 22. When the patient inhales and there is insufficient gas pressure in conduit 19, the flapper 7 under vacuum opens to allow air to pass from the vents 22, through the accumulation chamber 2 into the breathing chamber 8.

Anti-lockup valve 23 operates to prevent lock up of the patient diaphragm 5. The diaphragm 5 will lock up when pressure build up in the accumulation chamber 2, during the on cycle, behind the diaphragm 5 causes the diaphragm 5 to remain against it's seat 6 at the end of the on cycle, thus creating a high expiratory resistance for the patient. During the on cycle, pressure from conduit 24 causes piston 25 to move to the right against the bias of spring 144 closing off the gas outlets 26. At the end of the on cycle, pressure in conduit 24 instantly decays allowing the piston 25 to move to the left, as drawn under the spring 144 bias. The pressure in the accumulation chamber 2 is permitted to instantly decay passing through the flapper valve 141 and ports 26.

The basic operation of the transport ventilator breathing circuit has been described above. Following below is an explanation of the gas distribution and controls that enable the transport ventilator to operate in manual override mode, patient breathing demand mode and automatic mode, and particularly the inclusion of alarm means to notify the operator of dangerous conditions or important changes in the patient's status or device operation. Gas distribution circuits distribute gas between the regulator 13 and the gas accumulation chamber 2 under controlled conditions selectively via a manual circuit, a demand circuit and an automatic circuit. Controls are powered solely by the pressure differential between the pressurized gas from the regulator input port 14 and atmospheric pressure external to the device.

The controls monitor and control these gas distribution circuits and include the following gas pressure powered alarms:

breathing circuit integrity alarm for notifying the operator that an integrity condition has been detected in the breathing circuit, such as the face mask leaking or that the patient is breathing independently;

power fail alarm for notifying the operator that the source of pressurised gas depleted and has a pressure below a selected source input value; and pressure relief alarm for notifying the operator that the patient's airway is above the selected pressure relief value.

To prevent the patient's lungs from fully collapsing, the controls also include means to maintain continuous gas pressure above a selected minimum in the breathing chamber 8 and patient's airway.

Operating Logic Hierarchy

The transport ventilator includes controls and alarms which operate on the basis of the following logical sequence. Since all controls and alarms operate on gas pressure, with no other outside electric or mechanical power sources, it is critical that gas pressure be maintained at an appropriate minimum level and is continuously monitored. Of course, an unacceptably high gas pressure is also undesirable since the patient may be harmed and the device damaged.

1. Is a sufficient gas supply pressure present at the regulator? If not, the emergency air intake valve 11 allows external air to enter the patient face mask preventing suffocation as described above.

2. Is gas pressure below the minimum pressure necessary for proper operation of the transport ventilator? If so, the power fail alarm is activated.

3. Is the patient's airway pressure above a maximum allowable pressure? If so, excess gas is expelled activating a pressure relief alarm and reducing pressure within the device.

4. Automatic mode is generally left on. Automatic mode of operation is used as a default condition under normal conditions to ensure that the patient receives sufficient breathable gas at all times. An exception to this general rule is where the operator completely shuts off automatic mode to use manual mode alone or to allow the patient to breath independently. However, when automatic mode is left on, it may be overridden by activation of the manual mode and is also overridden when the patient begins breathing spontaneously. Automatic mode resumes when manual mode is deactivated (with a delay to automatic cycling re-start) and when the patient ceases breathing independently. Therefore such an exception would be encountered only when the operator desires a high degree of manual control and is very confident that shutting off automatic mode is appropriate, or when the patient's inspiratory effort is sufficient to cause the automatic cycling to cease.

5. Automatic mode consists of timed bursts of pressurized gas to mimic an inhale-exhale sequence. Between bursts of the automatic cycle and also when automatic mode is off, pressure within the breathing chamber 8 and patient airway can be maintained above a selected minimum airway pressure by a continuous airway pressure circuit. The maintenance of minimum airway pressure prevents lung collapse. If the airway pressure is above the maximum allowable set pressure, gas is expelled activating the pressure relief alarm and maintaining the pressure within the device and the patient's airway.

6. If the operator wishes to apply manual ventilation while automatic mode is on, the activation of manual mode overrides automatic mode. Automatic mode resumes following a timed delay when manual mode is deactivated.

7. If the patient begins breathing independently, the breathing circuit integrity alarm is deactivated by the negative pressure created by the patient's breathing cycle. The pressure in the control chamber 99 is kept at static circuit pressure until the patient inhales, which lowers the pressure in chamber 99 silencing the alarm. While automatic mode is on, the activation of demand mode overrides automatic mode. Automatic mode resumes, after a timed delay when demand mode is deactivated by the ceasing of independent breathing activity. The breathing circuit integrity alarm may be manually overridden by an operator once aware of the change in patient status. Use of this alarm override will release gas pressure in the circuit and cause the alarm to be silenced for a preselected delay period, such as 11 seconds while gas pressure builds up again in the circuit, at which time the alarm will reactivate. Further overriding of the alarm will repeat the alarm silence period.

8. If the face mask leaks significantly or falls off the patient, the breathing circuit integrity alarm is also activated. The leakage lowers pressure within the breathing chamber 8 below the breathing circuit alarm pressure, and activates the integrity alarm.

Standard Components

The transport ventilator device includes several standard pneumatic components such as valves, switches, reed alarms assembled into various circuits. Below is presented a detailed explanation of the operation of the standard components for the benefit of readers not fully familiar with this art to ensure full disclosure of the invention.

Internal Regulator Valve (13), as seen in FIG. 3, comprises a conventional hollow regulator body with threaded input port 14 mounted to the compressed oxygen gas cylinder 12 with attached external regulator 142 and supply hose 143. Lateral outlets supply pressurized gas to supply and control conduits 3, 15, 16 and 17. A central valve stem is mounted to a sliding piston. The piston is spring biased to move the valve stem closing the regulator valve as the pressure increases. The spring bias force is variable to calibrate the regulator.

Manual Switches (27, 32, 34) are used in the controls of the device. One example is the automatic mode on/off switch 27 seen at the top of FIG. 2. A manual button 28 is depressed to select between connecting the normally open input port 29 to one of the two side outlet ports. The manual button 28 is spring biased such that outlet port 30 (nearest the button 28) is normally closed and outlet port 31 (remote from button 28) is normally open. Two manual mode on/off switches 32 have their manually depressed buttons mechanically tied together with a bar 33 to allow simultaneous manual depression. In FIG. 3, (drawn to the center right) a breathing circuit override switch 34 is used to vent gas and reduce pressure in conduit 35.

Needle Valves (36, 65, 66, 130) such as for example demand valve control pressure needle valve 36 in FIG. 2 at top, are used through out the device to restrict flow between different parts of control circuits thereby allowing venting of the downstream portion of the circuit, pressure reduction in the downstream portion and increasing the time required to recover pressure after venting.

Figure 4:
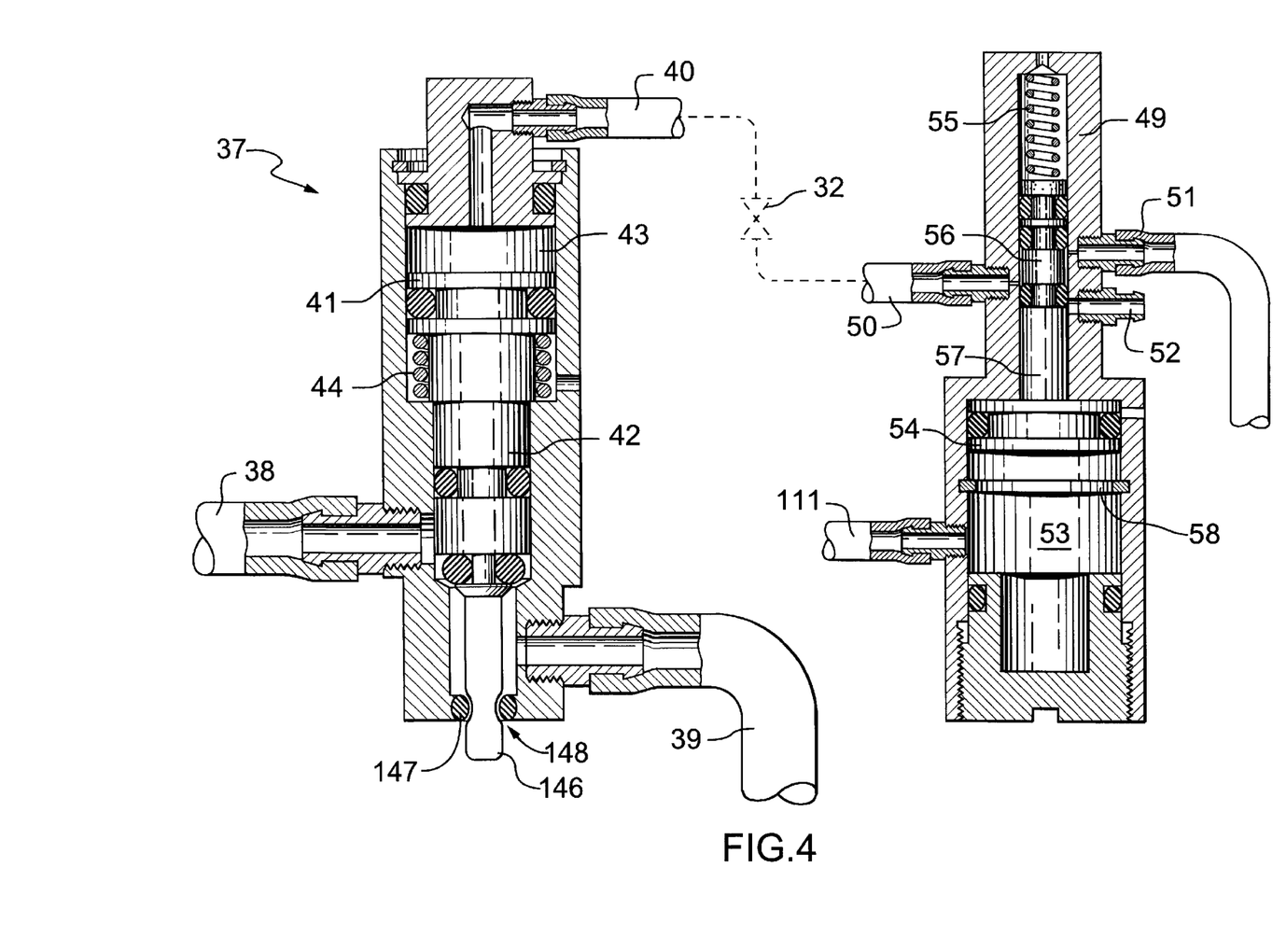
FIG. 4 is a detail sectional view of the automatic timing switch and high volume supply valve.

High Volume Pneumatic On/Off Switches (37, 45, 46, 47, 48) such as for example automatic main switch 37 in FIG. 4, selectively open and close the passage between conduits 38 and 39. Gas pressure supplied by conduit 40 to chamber 43 moves piston 41 and valve stem 42 downward against the bias of spring 44 to close the switch 37. Venting pressure from chamber 43 enables the spring 44 to open the switch 37. Identical high volume on/off switches are identified in FIG. 2 with numerals 45, and 46 and in FIG. 3 with numerals 47 and 48. Optionally, to release backpressure from conduit 39, the valve stem 42 can be extended with a tapered pin 146 which in conjunction with seal 147 alternately opens and closes an annular bottom vent 148.

Low Volume Pneumatic Two-Way Switches (49, 59, 60), such as for example automatic timing switch 49 in FIG. 4, selectively connects an open conduit 50 with one of two nipples 51 and 52. Gas pressure within chamber 53 moves piston 54 upward against the bias of spring 55 connecting conduit 50 and nipple 51 by allowing gas to pass around a reduced diameter portion 56 of the valve stem 57. Venting pressure within chamber 53 enables the spring 55 to force the piston downwardly against the limit ring 58, thereby positioning reduced portion 56 to connect conduit 50 and nipple 52. An identical low volume pneumatic two-way switch is identified in FIG. 3 with numeral 59. A modified input sensor/switch 60 is also shown in FIG. 3, wherein the opposite side of the piston is pressurized and the spring location is changed to bias the valve stem in an opposite direction.

Figure 5:
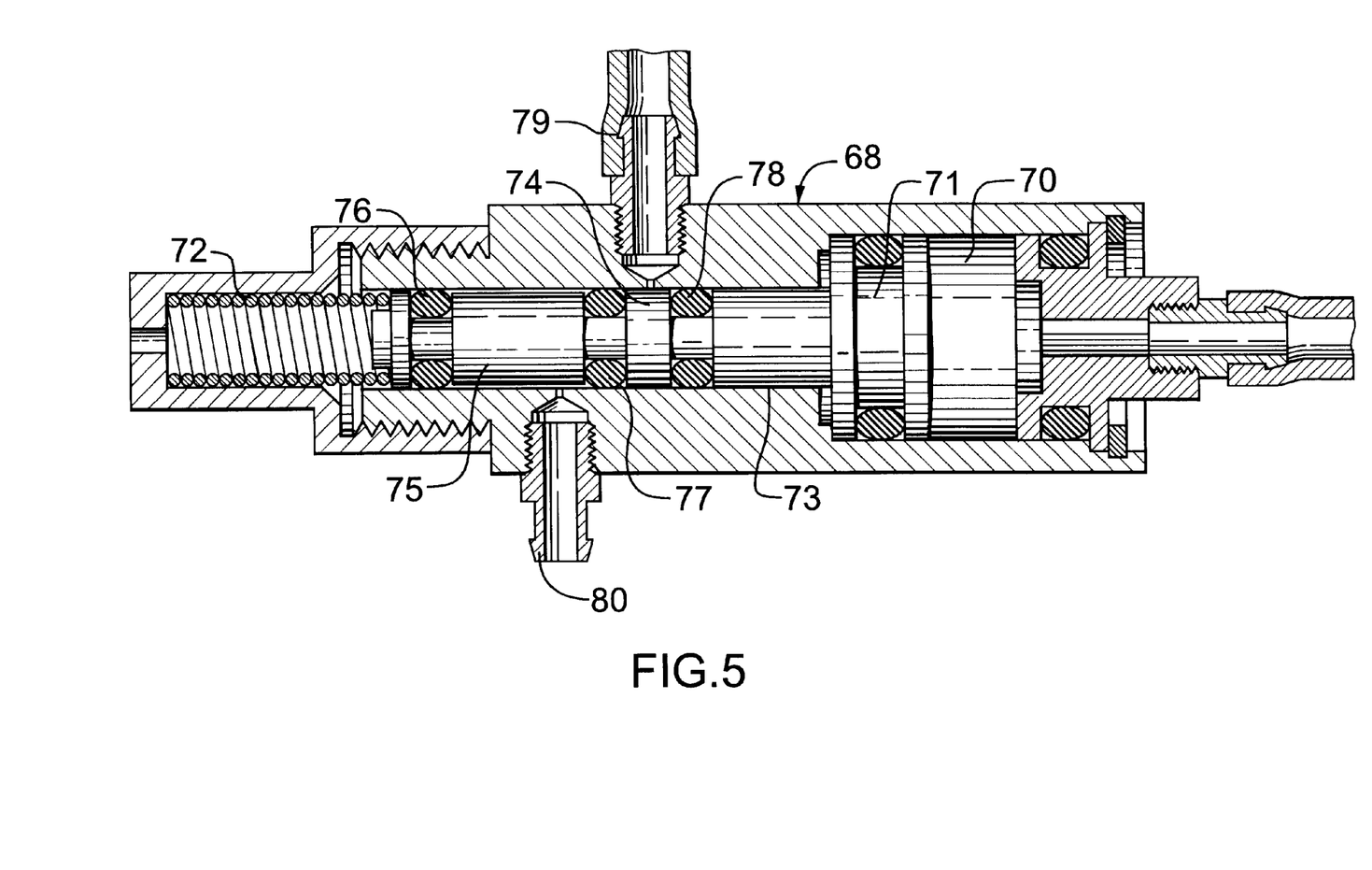
FIG. 5 is a sectional view of a low volume control valve.

Low Volume Pneumatic On/Off Switches (68, 69) seen in FIG. 2, and in detail in FIG. 5, are similar in construction and operation to the two way switches 49, 59 and 60 described above. Referring to FIG. 5, gas pressure in the chamber 70 forces piston 71 to the left against the bias of spring 72. The valve stem 73 includes two portion of reduced diameter 74 and 75 separated and sealed with O-rings 76, 77, and 78. In FIG. 5, the Off position is shown where passage between nipples 79 and 80 is prevented. Venting pressure from the chamber 70 permits the spring 72 to shift the stem 73 to the right thereby presenting reduced diameter portion 75 in a position to permit gas passage between nipples 79 and 80.

Reed Alarms (62, 63, 64) are powered by gas flow past the reed to produce an audible alarm signal to the operator. In FIG. 3 can be seen the power fail reed alarm 62, and the breathing circuit integrity reed alarm 63. In FIG. 2, the pressure relief reed alarm 64 is shown at the bottom right. Needle valves 65, and 66, shown in FIG. 3 immediately upstream of the reed alarms 62, and 63 provide slow release of pressurized gas through the reed alarms 62, and 63 to ensure that the operator's attention is directed to the alarm condition and to permit sound volume adjustment.

Filters (67) are placed throughout the circuits to prevent to prevent passage of microscopic particles which could impede operation of the control valves etc.

Figure 6:
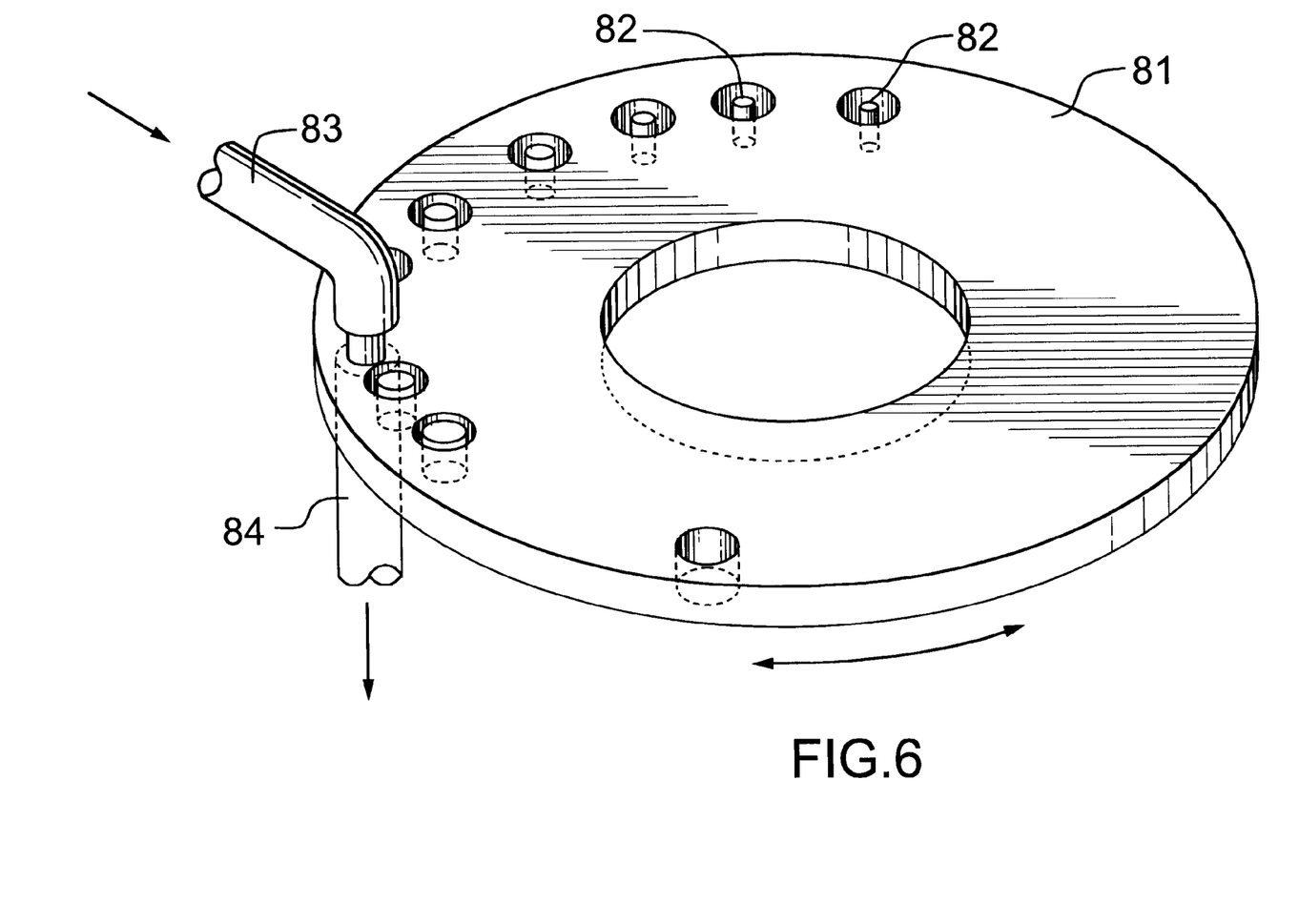
FIG. 6 is an exploded schematic view of a rotary disc valve used to control gas flow through associated stationary nozzles with a series of orifices of varying diameters.

Rotary Disc Valves (85, 86) are used for precise control over the timing frequency and flow quantity during the automatic mode. As shown in FIG. 6, this type of valve uses a plastic disc 81 which is mounted for manual rotation about its center. The disc 81 has a series of orifices 82 of varying diameter sizes spaced at regular radial intervals. An input nozzle 83 is mechanically registered into sealing engagement with the small and large orifices 82 with a sealing gasket (not shown) to permit passage of a predetermined flow of pressurized gas to output conduit 84. The orifices 82 are shown as countersunk to indicate that the nozzle 83 is mechanically registered into sealing engagement with the orifice 82 with O-rings for example. The orifices 82 are microscopic in diameter and are drilled using precise laser drilling techniques. In FIG. 2 are shown a rotary disc flow control valve 85, and a rotary disc frequency control valve 86.

Pressure Sensor Switches (87, 88 negative and positive respectively) are used to detect a change in pressure and to activate a switch as a result. A detailed view of a negative pressure sensor demand switch 87 is shown in FIG. 1, wherein the demand switch 87 is mounted immediately above the demand supply conduit 3. An airway positive pressure sensor switch 88 shown in FIG. 3 has a similar configuration, the operation of which is described in detail below under the heading Breathing Circuit Integrity Alarm.

Referring to detail FIG. 1, the negative pressure demand valve 87 has three functions.

(a) The first function is to permit passage of pressurized gas from the demand supply conduit 3 to the accumulation chamber 2, when the patient inhales independently (creating a negative pressure on inhalation) as follows.

The demand switch 87 is activated by patient inhalation which lowers gas pressure in the breathing chamber 8, drawing the flexible annulus 5 downward to rest on the valve seat 6, and opening the flapper valve 7. When the flapper valve 7 is opened, further inhalation by the patient reduces pressure in the accumulation chamber 2. Lower pressure in the accumulation chamber 2 also reduces pressure in the lower chamber 89 of the demand switch 87 due to communication through a connecting bore 90 in the housing 1. The flexible annulus 91 is drawn downwardly when the pressure in the lower chamber 89 is lower than atmospheric pressure in the upper chamber 92. The upper chamber communicates with atmosphere via openings 93.

Downward movement of the annulus 91 rotates rocker arm 94 clockwise to open nozzle 95. The rocker arm 94 is biased to close the nozzle 95 by the compression spring 96 and is accurately calibrated with set screw 97 on rocker support arm 98.

When nozzle 95 is closed, high pressure is maintained in the demand chamber 99 by gas supplied via control conduit 100. High pressure in the demand chamber 99 forces demand valve diaphragm 101 downward into sealing engagement with the demand valve seat 102. Therefore engagement of the diaphragm 101 and seat 102 prevents pressurized gas from passing from the demand supply conduit 3, over the seat 102 through radially spaced bores 103 to the accumulation chamber 2.

Opening of nozzle 95 vents gas from demand chamber 99 through the nozzle 95 and lowers pressure in the demand chamber 99. As a result, the upwardly biased diaphragm 101 lifts off the seat 102 to enable pressurized gas to pass from the demand supply conduit 3, over the seat 102 through bores 103 to the accumulation chamber 2.

(b) The second function of the negative pressure demand valve 87 is to actuate automatic cycle shutoff valve 69, to shut down the automatic cycle when the patient inhales independently. (A detailed explanation is presented below under the heading of Patient Breathing Demand Override Mode.)

(c) The third function of the negative pressure demand valve 87 is to actuate breathing circuit integrity alarm shutoff valve 69, to disable the breathing circuit integrity alarm 63 when the patient inhales independently. (A detailed explanation is presented below under the heading of Patient Breathing Demand Override Mode.)

Automatic Mode and Automatic Circuit

As stated above, normally the automatic mode is used as a default operating mode to provide a timed sequence of pressurized gas bursts in an inhale-exhale cycle. U.S. Pat. No. 5,520,170 provides a description of a similar automatic transport ventilator, however, several improvements have been made to the present invention.

Referring to FIGS. 2 and 3, the automatic gas distribution circuit conducts gas between the regulator 13 outlet via automatic supply conduit 15 and automatic distribution conduit 38 to the automatic main switch 37. The main switch 37 is opened and closed by the timing switch 49 at selected intervals (to be described in detail below) to produce an inhale-exhale cycle of gas bursts. Gas passes through the main switch 37 in conduit 39 to rotary disc flow control valve 85. A flow rate past the flow control valve 85 is selected by the operator manually rotating the perforated disc 81(see FIG. 6).

Gas flow from the rotary disc flow control valve 85 can take two alternative paths depending on whether the mixer switch 103 is set for normal flow through conduit 104 or mixed flow through conduit 105 and venturi mixer 106. Normal flow through conduit 104 consists of pure gas conveyed to the accumulation chamber 2 via automatic supply conduit 4 (see FIGS. 2 and detail of FIG. 1). Mixed flow consists of pure gas flow from the flow control valve 85 through conduit 105 to the mixer switch 103 to venturi mixer 106 where ambient air is drawn in and mixed with the gas before being conveyed to the accumulation chamber 2 through the automatic supply conduit 4.

Referring to FIGS. 2 and 4, the operation of the automatic main switch 37 and timing switch 49 will be described. As seen in FIG. 4, when pressurized gas is provided to the timing switch chamber 53, the valve stem is pushed upwardly to connect gas supply from nipple 51 to conduit 50. Pressurized gas from conduit 50 passes through normally open manual switch 32 through conduit 40 to fill chamber 43 in the automatic main switch 37. Pressure in the main switch chamber 43 moves the valve stem 42 to the closed position illustrated.

To open the automatic main valve 37, pressure in the chamber 53 of timing switch 49 is released and spring 55 forces the stem 57 downwardly. As a result pressurized gas from the chamber 43 of main switch 37 is vented through conduits 40 and 50 and exhausted through nozzle 52 to atmosphere.

The timing of pressurized gas to chamber 53 of timing switch 49 is accomplished as follows. As seen in FIG. 2, when gas is provided via conduit 39 to the input side of automatic flow control valve 85, a portion of the input flow is conducted through filter 67 via conduit 107 to the rotary disc frequency control valve 86. The frequency control valve 86 also includes the structure illustrated in FIG. 6, wherein a selected orifice 82 provides a controlled gas flow through the valve 86. It is important to note that frequency control valve 86 and flow control valve 85 can be controlled separately in order to allow gas flow and timing frequency to be independently selected.

To pressurize chamber 53 of the timing switch 49, gas flows from the main automatic switch 37 through flow control valve 85 to the frequency control valve 86, then through conduit 108, manifold 109, and conduit 110 to the manual automatic mode on/off switch 27. Since the switch 27 is normally open, gas flows through nozzle 31 and conduit 111 to chamber 53 of the timing switch 49. Pressurizing the chamber 53 forces the valve stem 57 of the timing switch 49 up, pressurizes chamber 43 of the main valve 37 and closes the main valve 37.

Therefore, opening of the main valve 37 provides the pressurized gas to close the main valve 37, via the frequency control valve 86 and timing switch 49. The time delay between main valve opening and closing is controlled primarily by the selection of a flow restricting orifice 82 in the frequency control valve 86, although delay also results from further head losses in flow passing through the automatic circuit as described above. Variable volume chamber 145 also provides fine control over timing adjustment. The larger the volume in chamber 145 is, the longer it takes for pressure to build up in chamber 53. By adjusting the volume in chamber 145, the cycle time of timing switch 49 can be adjusted.

Manual Override Mode

The operator may wish under certain conditions to manually administer bursts of pressurized gas. This is accomplished by manually controlling the opening and closing of the main valve 37, and overriding the timed sequencing of the automatic mode circuit.

Automatic mode may be manually turned on and off by depressing the button 28 on switch 27. By depressing the button 28, pressurized gas is permitted to pass from the control manifold 18 to (otherwise normally closed) nozzle 30 through switch 27 to nozzle 31 and conduit 111. Gas pressure in conduit 111 pressurizes the chamber 53 of timing switch 49 to circuit static pressure which is approximately 2 times higher than normal cycling pressure which creates a delay for automatic cycling re-start upon releasing manual switch valve 32.

With reference to FIG. 2, the main valve 37 is manually opened and closed by depressing the bar 33 of manual mode on/off switches 32. The operation of the manual switch 32 drawn to the left, exhausts gas from the main switch 37 chamber 43 via conduit 40 through (otherwise normally closed) nozzle 112 to atmosphere. In the event that automatic mode remains on, (i.e. switch 27 has not been manually depressed to an off position) simultaneous depression of the button on the right manual switch 32 injects gas from the manifold 18 through conduit 113 to conduit 114, through manifold 109, conduit 110 and normally open nozzle 29 to pressurize the chamber 53 of timing switch 49 thereby shutting off and overriding the automatic timed sequence, and creating a delay for automatic cycling re-start.

Patient Breathing Demand Override Mode

As noted above, with reference to FIG. 1, the negative pressure demand valve 87 is used to permit passage of pressurized gas from the demand supply conduit 3 to the accumulation chamber 2, when the patient begins breathing independently. The demand switch 87 is activated when the patient inhales. This results in lower/negative gas pressure in the breathing chamber 8 which draws the flexible annulus 5 downward to rest on the valve seat 6, and opens the flapper valve 7. Further inhalation reduces pressure in the accumulation chamber 2, which reduces pressure in the lower chamber 89 of the demand switch 87 due to communication through a bore 90 in the housing 1. The flexible annulus 91 is drawn downwardly when the pressure in the lower chamber 89 is lower than atmospheric pressure in the upper chamber 92. The upper chamber communicates with atmosphere via openings 93.

Downward movement of the annulus 91 rotates rocker arm 94 clockwise to open nozzle 95. The rocker arm 94 is biased to close the nozzle 95 by the compression spring 96 and is calibrated with set screw 97 on rocker support arm 98. When nozzle 95 is closed, high pressure is maintained in the demand chamber 99 by gas supplied via control conduit 100. High pressure in the demand chamber 99 forces demand valve diaphragm 101 downward into sealing engagement with the demand valve seat 102. Therefore engagement of the diaphragm 101 and seat 102 prevents pressurized gas from passing from the demand supply conduit 3, over the seat 102 through radially spaced bores 103 to the accumulation chamber 2. Opening of nozzle 95 vents gas from demand chamber 99 through the nozzle 95 and lowers pressure in the demand chamber 99. As a result, the upwardly biased diaphragm 101 lifts off the seat 102 to enable pressurized gas to pass from the demand supply conduit 3, over the seat 102 through bores 103 to the accumulation chamber 2.

Low pressure in conduit 100 results in the spring biased pistons of automatic cycle shutoff valve 69 and breathing circuit integrity alarm shutoff valve 68 to shifting to the right as drawn.

Regarding the automatic cycle shutoff valve 69 shown in FIG. 5, it can be seen that low pressure in chamber 70 (caused by patient inhaling leading to low pressure in chamber 99 as described above) allows the spring 72 to force the valve stem 73 right and permit gas to flow between nipples 79 and 80. In the case of valve 69 gas flow from manifold 18 through conduit 133 then flows to conduit 134, manifold 109, conduit 110, open switch 27, conduit 111 to chamber 53 of the timing switch 49 to shut main automatic switch 37. In this way the automatic timed mode is overridden when the patient inhales, and creating a delay for automatic cycling re-start.

Regarding the breathing circuit integrity alarm shutoff valve 68 (which is similar in construction to valve 69 shown in FIG. 5), low pressure in chamber 99 allows pressure to be vented from conduit 149 to shut off the breathing circuit integrity alarm 63.

Breathing Circuit Integrity Alarm

The breathing circuit integrity reed alarm 63 (FIG. 3) is activated when the patient ceases to inhale independently on demand mode, or when the face mask leaks or falls off the patient. This result is accomplished by maintaining gas pressure in the patient breathing circuit above or below a selected maximum or minimum airway pressure. This minimum airway pressure is above atmospheric pressure, and a breathing circuit integrity condition is detected whenever the gas pressure in the patient breathing circuit drops below the minimum airway pressure to atmospheric or lower or negative pressure triggers valve 68 to open to atmosphere deactivating the alarm.

Referring to FIGS. 2 and 3, continuous patient airway pressure (CPAP) is maintained as follows. High volume pressurized gas is supplied via automatic supply conduit 15 to CPAP conduit 115. The CPAP circuit operates in tandem with the automatic mode circuit described above. When the main valve 37 is open, gas is supplied to the input side of flow control valve 85 by conduit 39. A portion of that input flow is conducted via conduit to the chambers 43 (see typical example high volume switch 37 in FIG. 4) of high volume CPAP switches 45 and 46. Therefore, when main switch 37 is open, CPAP switches 45 and 46 are closed. When main switch 37 is closed (by timing switch 49, or when automatic mode is off or overridden) CPAP switches 45 and 46 are opened.

Opening of CPAP switch 45 permits gas to pass from conduit 115 to conduit 117 and into the CPAP needle control valve 118. The control valve 118 is set to determine the minimum airway pressure of gas which passes through CPAP valve 46 through conduit 119 to the breathing chamber 8 (see FIG. 1). The purpose of the second CPAP valve 46 is to prevent decay of gas pressure from the breathing chamber 8, and to prevent decay of gas from the conduit 117 and CPAP needle valve 118, both of which would detrimentally effect the performance of the inhale/exhale cycle peak pressures.

Referring to FIGS. 2 and 3, the breathing chamber 8 connects to an adapter 120 and face mask nozzle 121 (indicated by dashed lines in exploded view). Positive patient airway pressure is sensed by the airway pressure sensor switch 88 via conduit 122 and visually indicated with barometer 123. Since the internal mechanism of airway positive pressure sensor switch 88 operates in a similar manner (but in reverse) to the negative pressure sensor demand switch 87 described above, a detailed explanation of operation is considered unnecessary. Gas pressure imbalance between chambers on either side of the flexible diaphragm 91 will move the diaphragm towards the low pressure side and throw the switch.

An airway pressure greater than the preset minimum airway pressure in the patient's airway and conduit 122 will cause gas to depress the flexible annulus of switch 88, exhausting gas through vent 124 and keeping nozzle 125 open as drawn. When nozzle 125 is kept open, pressure in conduit 126 is kept low, thereby maintaining switch 59 with piston in a downward position. Gas then flows from the manifold 18 through conduit 127 to conduit 128 and results in closing switch 48. With switch 48 closed, gas cannot pass from breathing circuit integrity alarm supply conduit 16 to the breathing circuit integrity reed alarm 63.

An airway pressure lower than the preset minimum positive airway pressure, can be caused by various integrity conditions, such as the face mask leaking or falling off the patient's face. Low pressure in conduit 122 will permit the flexible annulus of switch 88 to rise under spring bias to close the nozzle 125. As a result, pressure within conduit 126 will rise as gas is supplied slowly from the manifold 18 via conduit 129 and flow restricting needle valve 130. High pressure in conduit 126 causes the valve stem of switch 59 to move upwardly as drawn connecting conduit 128 to conduit 131. As a result, the chamber of switch 48 is vented, and gas is permitted to pass from conduit 16 to the breathing circuit integrity reed alarm 63. An audible signal is provided to the operator as the gas is vented to atmosphere through the reed alarm 63. Integrity reed alarm 63 oscillates rapidly and emits a high frequency tone to allow for user differentiation of the alarm condition from other alarms. The back pressure generated by needle valve flow restrictor 66 directs gas through conduit 131 to 128 to switch 48 thereby closing off flow from conduit 16 to reed alarm 63. Gas in switch 48 then decays back through conduit 128 to conduit 131 and through reed alarm 63. Switch 48 opens again and the cycle repeats itself creating a rapid oscillating high pitch alarm signal.

The operator may manually override and disable the breathing circuit integrity alarm 63 by reducing pressure in conduit 126 and closing the switch 48. This is done by depressing the button 132 of breathing circuit override switch 34 to open the normally closed connection to conduit 35 and venting the gas to atmosphere.

Power Fail Alarm

The transport ventilator includes a power fail reed alarm 62, shown in FIG. 3, which notifies the operator that the source of pressurized gas (cylinder 12, regulator 142, supply hose 143) has a pressure below a selected source input value, which is a minimum required for safe operation of the device.

Referring to FIG. 3, an input pressure switch 60 is provided to sense the gas pressure at the regulator input port via conduit 135. When pressure in conduit 135 is extremely high the piston in switch 60 is pushed upward against the force of the spring shown.

When pressure is above the preset value, piston in switch 60 is shifted upward to allow gas to pass from the manifold 18 via conduit 136 through the switch 60 to conduit 137. High pressure in conduit 137 moves the piston in valve 47 down to close the flow of gas between conduit 138 and the power fail alarm 62.

When pressure in the cylinder 12 and conduit 135 is low, the spring in switch 60 shifts the piston down as drawn and vents gas from conduit 137 through conduit 139 and the power fail alarm 62. Venting of gas from conduit 137 causes the piston in switch 47 to move upward and opens a path for gas to flow from conduit 138 through switch 47 to the power fail reed alarm 62. Although gas pressure is relatively low when the power fail alarm 62 is activated, gas flow through conduit 138 is sufficient to power the audible reed alarm 62 for a period of time to notify the operator that gas supply is low. Switch 47 slowly oscillates (with a medium frequency tone) and the oscillations gradually decay to a constant tone as the cylinder 12 contents deplete.

Pressure Relief Alarm

The pressure relief alarm is used to notify the operator that pressurized gas is being expelled from the device since pressure above a selected maximum relief value has been detected in the patient's airway.

Excessive airway pressure may harm the patient and damage circuits of the device. As shown in FIGS. 2 and 3, the breathing chamber 8 is connected to an adapter 120 and face mask nozzle 121. Also provided in connection with the breathing chamber 8 is an adjustable pressure relief switch 140 for sensing gas pressure in the breathing circuit. When an excessively high pressure is sensed the pressure relief switch 140 opens to expel gas from the breathing chamber 8 through the audible pressure relief reed alarm 64. The pressure relief switch 140 is adjustable to actuate within a range of selected relief values in mechanical connection with the rotary disc 81 of the flow control valve 85.

As a result, the invention provides an improved transport ventilator device which includes gas powered sensors and alarms to notify the operator of breathing circuit integrity conditions, power failure and pressure relief conditions.

Although the above description and accompanying drawings relate to a specific preferred embodiment as presently contemplated by the inventors, it will be understood that the invention in its broad aspect includes mechanical and functional equivalents of the elements described and illustrated.

The embodiments of the invention in which an exclusive property or privilege is claimed are defined as follows:

1. A transport ventilator device for administering a breathable gas under pressure to a patient by an operator, the device having controls powered by said pressurised gas in a manual override mode, a patient breathing demand override mode, and an automatic mode, the device comprising:
   a housing enclosing a patient breathing circuit comprising: a gas accumulation chamber; a breathing chamber; breathing check valve means therebetween for permitting one way passage of inhaled gas from the accumulation chamber to the breathing chamber; and exhale check valve means for permitting passage of patient exhaled breath from the breathing chamber to atmosphere external to the device;
   a pressure regulator having regulator input port means for admitting said gas into the device from a source of pressurised gas, and having a regulator outlet;
   gas distribution means for distributing gas between the regulator outlet and the gas accumulation chamber selectively via a manual circuit, a demand circuit and an automatic circuit wherein the automatic circuit includes:
      an automatic distribution conduit between the regulator outlet and the gas accumulation chamber, and wherein the control means includes:
      timing switch means for opening and closing the automatic distribution conduit at selected intervals;
      frequency control means for actuating the timing switch means at a predetermined timing cycle corresponding to a patient inhale-exhale breathing pattern; and
      flow control means for selecting a predetermined gas flow rate through the automatic distribution conduit independently of the timing cycle;
   control means, powered solely by the pressure differential between the pressurised gas from the regulator input port means and atmospheric pressure external to the device, for monitoring and controlling said gas distribution means, wherein the control means include pressurised gas powered alarm means selected from the group consisting of:
      breathing circuit integrity alarm means for notifying the operator that an integrity condition has been detected;
      power fail alarm means for notifying the operator that the source of pressurised gas has a pressure below a selected source input value; and
      pressure relief alarm means for notifying the operator that the patient's airway is above the selected pressure relief value.

2. A device according to claim 1 wherein the control means includes continuous patient airway pressure means for maintaining gas pressure in the patient breathing circuit above a selected minimum airway pressure.

3. A device according to claim 2 wherein the control means includes patient airway pressure sensor means for sensing the gas pressure in the patient breathing circuit and for activating the breathing circuit integrity alarm means when the pressure is below a selected breathing circuit alarm pressure.

4. A device according to claim 3 wherein the patient airway pressure sensor means includes breathing circuit integrity alarm switch means for conducting gas from the gas distribution means through an audible breathing circuit integrity reed alarm to atmosphere.

5. A device according to claim 3 wherein the control means includes a breathing circuit integrity alarm override means for manually selectively disabling the breathing circuit integrity alarm means.

6. A device according to claim 1 wherein the power fail alarm means includes input pressure switch means for sensing the gas pressure at the regulator input port means, and for conducting gas from the gas distribution means through an audible power fail reed alarm to atmosphere.

7. A device according to claim 1 wherein the pressure relief alarm means includes pressure relief switch means for sensing the gas pressure in the patient breathing circuit, and for expelling gas from the patient breathing circuit through an audible pressure relief alarm to atmosphere.

8. A device according to claim 7 wherein the pressure relief switch means is adjustable to actuate within a range of selected relief values.

9. A device according to claim 1 wherein the control means includes continuous patient airway pressure means for maintaining gas pressure in the patient breathing circuit above a selected minimum airway pressure when the timing valve is closed.

10. A device according to claim 1 wherein the automatic circuit includes mixing means within the automatic distribution conduit for mixing ambient air with the pressurised gas.

11. A device according to claim 10 wherein the mixing means comprise a venturi mixer with ambient air inlet check valve means for permitting one way passage of air into the venturi mixer and for preventing escape of pressurised gas from the automatic distribution conduit to atmosphere.

12. A device according to claim 1 wherein the flow control means comprise:
   a flow control nozzle; and
   flow control port means comprising a plurality of separate flow control orifices of varying sizes movably mounted in relation to the flow control nozzle and a selected one of said flow control orifices being adapted to be selectively registered with the flow control nozzle for selecting a predetermined gas flow rate.

13. A device according to claim 1 wherein the frequency control means comprise:

a frequency control nozzle; and frequency control port means comprising a plurality of separate frequency flow orifices of varying sizes movably mounted in relation to the frequency control nozzle and a selected one of said frequency flow orifices being adapted to be selectively registered with the frequency control nozzle for selecting a predetermined timing valve frequency.

* * * * *